United States Patent
Ogle et al.

(10) Patent No.: US 6,302,909 B1
(45) Date of Patent: Oct. 16, 2001

(54) CALCIFICATION-RESISTANT BIOMATERIALS

(75) Inventors: Matthew F. Ogle, St. Paul; Richard F. Schroeder, Oakdale, both of MN (US)

(73) Assignee: St. Jude Medical, Inc., St. Paul, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/690,661

(22) Filed: Jul. 31, 1996

(51) Int. Cl.⁷ .......................................... A61F 2/02
(52) U.S. Cl. .................. 623/1.42; 623/2.42; 623/901; 623/925; 8/94.11; 427/2.24
(58) Field of Search ............... 623/1, 2, 11, 901, 623/1.42, 1.45, 2.42, 916, 917, 921, 925; 8/94.11; 427/2.24, 2.25

(56) References Cited

U.S. PATENT DOCUMENTS

| | | |
|---|---|---|
| 4,167,045 | 9/1979 | Sawyer . |
| 4,378,224 | 3/1983 | Nimni et al. . |
| 4,402,697 * | 9/1983 | Pollock et al. .................. 8/94.11 |
| 4,753,652 | 6/1988 | Langer et al. . |
| 4,770,665 | 9/1988 | Nashef . |
| 4,798,611 | 1/1989 | Freeman, Jr. . |
| 5,002,566 * | 3/1991 | Carpentier et al. .............. 623/11 |
| 5,094,661 * | 3/1992 | Levy et al. ...................... 623/2 |
| 5,104,405 | 4/1992 | Nimni . |
| 5,133,956 | 7/1992 | Garlich et al. . |
| 5,215,541 | 6/1993 | Nashef et al. . |
| 5,368,608 * | 11/1994 | Levy et al. ...................... 623/2 |
| 5,443,813 | 8/1995 | Hainfeld . |
| 5,509,932 * | 4/1996 | Keogh et al. .................... 623/11 |
| 5,697,967 * | 12/1997 | Dinh et al. ...................... 600/36 |
| 6,013,106 * | 1/2000 | Tweden et al. ................... 623/11 |

FOREIGN PATENT DOCUMENTS

| | | |
|---|---|---|
| 0 121 008 A2 | 10/1984 | (EP) . |
| 86/00795 * | 2/1986 | (WO) ........................ 427/2.24 |
| WO 88/01155 | 2/1988 | (WO) . |
| WO 94/01481 | 1/1994 | (WO) . |
| WO 95/11047 | 4/1995 | (WO) . |

OTHER PUBLICATIONS

Bamberger et al., "Inhibition of Alkaline Phosphatase by Beryllium and Aluminum", Archives of Biochemistry and Biophysics, 123:195–200 (1968).

Joshi et al., "Ferritin: An Iron Storage Protein With Diverse Functions", BioFactors, vol. 1, No. 3, pp. 207–212 (1988).

Levy et al., "Initiation of Mineralization in Bioprosthetic Heart Valves: Studies of Alkaline Phosphatase Activity and its Inhibition by $AlCl_3$ or $FeCl_3$ Preincubations", J. Biomed. Mater. Res., 25:905–935 (1991).

Meldrum et al., "Synthesis of Inorganic Nanophase Materials in Supramolecular Protein Cages", Nature, vol. 349, pp.684–686 (1991).

Spiro et al., "The Hydrolytic Polymerization of Ferric Citrate. I. The Chemistry of the Polymer", J. Am. Chem. Soc., 89:5555–5559 (1967).

Johnston et al., Journal of Pharmaceutical Sciences, vol. 77, No. 9, pp. 740–744 (Sep. 1988).

Vyavahare et al., Journal of Controlled Release, vol. 34, No. 2, pp. 97–108 (May 1995).

Webb et al., ASAIO Transactions, vol. 34, No. 3, pp. 851–854 (Jul./Sep. 1988).

Webb et al., ASAIO Transactions, vol. 36, No. 3, pp. 408–410 (Jul./Sep. 1990).

* cited by examiner

Primary Examiner—Paul B. Prebilic
(74) Attorney, Agent, or Firm—Hallie A. Finucane, Esq.; Patterson, Thuente, Skaar & Christensen, P.A.; Peter S. Dardi, Ph.D.

(57) ABSTRACT

The invention involves a bioprosthetic article including a biocompatible material having at least one bound exogenous storage structure, the storage structures having collectively greater than about 0.5 mg metal cations per gram of biocompatible material. The calcification inhibitors preferably decrease calcium deposition by greater than 95% relative to untreated tissue. The calcification inhibitors are bonded to the bioprosthetic material preferably at a pH between about 6.0 and 8.5.

24 Claims, No Drawings

CALCIFICATION-RESISTANT BIOMATERIALS

BACKGROUND OF THE INVENTION

The invention relates to prosthetic material that is treated to reduce calcification. More particularly, the invention relates to prosthetic material which is complexed with slowly released calcification inhibitors.

Bioprostheses, i.e., bioprosthetic devices, are used to repair or replace damaged or diseased organs, tissues and other structures in humans and animals. Bioprostheses must be generally biocompatible since they are typically implanted for extended periods of time. Specifically, bioprostheses can include artificial hearts, artificial heart valves, ligament repair material, vessel repair, surgical patches constructed of mammalian tissue and the like. Bioprostheses can be constructed from a combination of natural or synthetic materials.

Calcification, i.e., the deposit of calcium salts especially calcium phosphate (hydroxyapatite), occurs in and on some materials used in the production of implantable bioprostheses. This affects the performance and structural integrity of medical devices constructed from these biomaterials, especially over extended periods of time. For example, calcification is the primary cause of clinical failure of bioprosthetic heart valves made from porcine aortic valves or bovine pericardium. Calcification also significantly affects the performance of bioprostheses constructed from synthetic materials, such as polyurethane.

The importance of bioprosthetic animal heart valves as replacements for damaged human heart valves has resulted in a considerable amount of attention directed to the effects of calcification on these xenotransplants. Bioprosthetic heart valves from natural materials were introduced in the early 1960's and are typically derived from pig aortic valves or are manufactured from other biological materials such as bovine pericardium. Xenograft heart valves are typically fixed with glutaraldehyde prior to implantation to reduce the possibility of immunological rejection. Glutaraldehyde reacts to form covalent bonds with free amino groups in proteins, thereby chemically crosslinking nearby proteins.

Generally, bioprosthetic heart valves begin failing after about seven years following implantation, and few bioprosthetic valves remain functional after 20 years. Replacement of a degenerating valve prosthesis subjects the patient to additional surgical risk, especially in the elderly and in situations of emergency replacement. While failure of bioprostheses is a problem for patients of all ages, it is particularly pronounced in younger patients. over fifty percent of bioprosthetic valve replacements in patients under the age of 15 fail in less than five years because of calcification.

Similarly, calcification of polyurethane bladders in artificial hearts and of leaflets in polyurethane valves is potentially clinically significant. Other bioprostheses made from natural and/or synthetic materials display clinically significant calcification.

As a result, there is considerable interest in preventing the deposit of calcium on implanted biomaterials, especially heart valves. Research on the prevention of calcification has focused to a considerable extent on the pretreatment of the biomaterial prior to implantation. Detergents (e.g., sodium dodecyl sulfate), toluidine blue or diphosphonates have been used to pretreat tissues in an attempt to decrease calcification by reducing calcium nucleation. These materials tend to wash out of the bioprosthetic material rather rapidly into the body fluids surrounding the implant, limiting their effectiveness.

Another approach to reducing calcification has been to remove at least some of the reactive glutaraldehyde moieties from the tissue by a chemical process. Still other approaches have included development of alternative fixation techniques, since evidence suggests that the fixation process itself contributes to calcification and the corresponding mechanical deterioration. In addition, since nonviable cells present in transplanted tissue are sites for calcium deposition, various processes have been developed to remove cellular material from the collagen—elastin matrix of the tissue prior to implantation.

A significant advance toward reducing calcification of bioprostheses was the determination that $Al^{+3}$ cations and other multivalent cations inhibit calcification. Bioprosthetic materials were treated with an acidic, aqueous solution of $AlCl_3$ prior to implantation. While some of the $Al^{+3}$ cations wash away after being removed from the treatment solution, a significant amount of cations remain associated with the treated materials for extended periods of time, presumably due to some type of association of the cations with the bioprosthetic material. It appears that the loading of ions into the material reaches a limiting value.

The associated $Al^{+3}$ cations are found to contribute to significant inhibition of the deposit of calcium. Furthermore, this effect persisted over a significant period of time, at least several months in a juvenile animal. Treatment with $Fe^{+3}$ salts is observed to produce similar effectiveness in reducing calcification.

It has been proposed that alkaline phosphatase is involved in the calcification of bioprostheses. Calcification seems related to cellular destruction and the corresponding disruption of cellular calcium regulation that maintains low intracellular calcium concentrations due to the pumping of $Ca^{+2}$ out of the cell. Cellular damage results from mechanical damage, extreme pH, extreme ionic concentration and/or chemical fixation, such as glutaraldehyde treatment. The cellular damage results in an uncontrolled influx of calcium into the nonviable cells.

Physiologically normal calcification of skeletal and dental tissues and pathological calcification, such as calcification of bioprostheses, have important similarities including the initial deposit of apatitic mineral. These mineral deposits contain calcium and phosphates, and mineral growth takes place at nuclei provided by initial deposits. Nucleation in bone development takes place at structures that have a high concentration of calcium binding phospholipids and high activity of phosphatases, especially alkaline phosphatase. Alkaline phosphatase activity is particularly high in children, which may contribute to the severe calcification problem for bioprostheses implanted into young patients.

Phosphatase activity is found to be inhibited by incubation with $AlCl_3$ and $FeCl_3$. This result suggests that the effect of $Al^{+3}$ and $Fe^{+3}$ cations in reducing calcification is due to the inhibition of the phosphatase activity. Alternatively or in addition, the ions may act by substitution into the hydroxyapatite crystal lattice which could prevent growth by destabilizing the crystal.

SUMMARY OF THE INVENTION

In a first aspect, the invention involves a bioprosthetic article including a biocompatible material having at least one bound exogenous storage structure, the storage structures collectively having greater than about 0.5 mg metal cations per gram of biocompatible material releasably bound thereto. More preferably, the storage structures collectively have greater than about 10.0 mg metal cation per gram of biocompatible material. Even more preferably, the storage structures collectively have greater than about 15.0 mg metal cation per gram of biocompatible material.

Preferred metal cations include $Al^{+3}$, $Fe^{+3}$, or mixtures thereof. A preferred exogenous storage structure comprises ferritin. The biocompatible material can comprise mammalian tissue. Natural tissue, generally, can be selected from the group consisting of heart valves, roots, walls, leaflets, pericardial tissue, cartilage bypass grafts, tendons, ligaments, skin patches, blood vessels and umbilical tissue. The tissue can be a repopulated, resorbable matrix. Suitable biocompatible material includes porcine heart valves or portions thereof and bovine pericardium.

In another aspect, the invention involves a bioprosthetic article including natural tissue having at least one bound exogenous storage structure, the storage structures having a quantity of calcification inhibitors releasably bound thereto and the natural tissue having calcium deposition reduced by greater than 95 percent relative to equivalent natural tissue without the bound exogenous storage structures after approximately two months of subcutaneous implantation within a mammal. The exogenous storage structures preferably include ferritin. The calcification inhibitor preferably includes $Al^{+3}$ cations. Preferred biocompatible material includes porcine heart valves or portions thereof.

In another aspect, the invention involves a method of producing a bioprosthetic article including the step of binding ferritin to natural tissue, where the ferritin is loaded with calcification inhibiting metal cations such that there are at least 0.5 mg of metal cations per gram of the natural tissue. The metal cations can include $Al^{+3}$ cations. The binding can be accomplished by covalent or noncovalent bonding of the ferritin to the natural tissue. The bonding can be performed by contacting the loaded ferritin and the natural tissue with a solution comprising glutaraldehyde. The bonding can also be performed by forming antibody-antigen linkages.

In another aspect, the invention involves a method of producing a bioprosthetic article including the step of chemically binding a calcification inhibitor to a bioprosthetic material at a pH between about 6.0 and about 8.5. The calcification inhibitor can include an exogenous storage structure having a quantity of calcification inhibitors releasably bound thereto.

DETAILED DESCRIPTION

Bioprostheses of the invention are constructed from biocompatible material that have bound structures that store calcification inhibiting agents. The slow release of these agents from the storage structures over time inhibits the deposit of calcium salts, especially calcium phosphate, on the biocompatible material. The use of bound storage structures containing the calcification inhibiting agents provides considerable versatility through selection of particular storage structures and bound calcification inhibiting agents.

Any degree of inhibition of calcium deposition is useful, given the clear association between calcification and deterioration of bioprostheses. A preferred degree of inhibition reduces the calcium deposition by at least about 50 to 75 percent over a two month period, compared to an untreated bioprosthesis. A more preferred degree of inhibition reduces the calcium deposition by at least 90 percent and even more preferably by at least 95 percent after about two months of implantation.

The methods of preparing the biocompatible materials with the storage structures can use conditions approximating physiological conditions. Depending on the selection of the storage structure and the attachment of the storage structures to the biocompatible material, amounts of calcification inhibitor in the bioprosthesis matrix can be relatively very large. For metal cations, preferred loadings have greater than about 0.5 mg of ions per gram of dry tissue, more preferably greater than about 10 mg ions per gram of dry tissue and even more preferably greater than about 15 mg ions per gram of dry tissue. The calcification inhibiting agents generally can be selected to inhibit calcium formation and specifically can be selected to inhibit the action of enzymatic precursors to hydroxyapatite formation, such as alkaline phosphatase. A plurality of different storage structures holding one or more calcification inhibitors can be used in a single bioprosthesis.

A. Biocompatible Materials

A bioprosthesis (bioprosthetic article) of the present application is a device that is implanted within the body of a host human or animal. The bioprosthesis is made from one or more biocompatible materials, and may be suitable for long term implantation within the host. It may be useful to provide the host with immuno suppressant treatments, although this treatment often will not be necessary. At least one of these biocompatible materials may have bound storage structures. The storage structures store a quantity of a calcification inhibiting agent or agents.

The biocompatible material preferably includes biological material or polymeric material. Some prostheses may be composed completely of metal components, and these prostheses generally will not be relevant for this invention. Bioprostheses within the invention may be comprised of a mixture of materials, such as metal portions along with portions of biological material and/or synthetic polymers. Relevant bioprostheses include without limitation artificial hearts, artificial heart valves, ligament repair material, bypass grafts, surgical patches constructed of mammalian tissue, and the like.

Biological material for use in the invention includes relatively intact tissue as well as decellularized tissue. These tissues may be obtained from, for example, heart valves, portions of heart valves such as roots, walls, and leaflets, and pericardial tissues such as pericardial patches, connective tissue such as dura mater, homograft tissue, bypass grafts, tendons, ligaments, skin patches, blood vessels, cartilage, human umbilical tissue, and the like. Generally, the tissues include collagen-containing material derived from different animal species, typically mammalian, such as human, bovine, porcine, seal, and kangaroo, and tissue engineered material. Tissue engineered material involves a repopulated, resorbable matrix, which takes the form of a synthetic tissue. The biological tissue is typically but not necessarily soft tissue. Tissue samples are typically fixed to cross-link the tissue and provide mechanical stabilization by preventing enzymatic degradation of the tissue, although the samples do not need to be fixed. Glutaraldehyde is typically used to fix the cells, but other fixatives can be used, such as epoxides and other difunctional aldehydes.

Decellularized tissue can be produced that is composed primarily of a structural matrix with cellular material removed, such as the collagen and elastin structural matrix. The decellularization process can involve applications of enzymes, other chemicals and physical treatments. See, for example, copending U.S. patent application Ser. No. 08/424, 218, incorporated in its entirety by reference herein.

Synthetic, biocompatible polymeric materials for use in bioprostheses of the present invention include synthetic polymers as well as purified and woven biological polymers. Synthetic polymers include polyamides (nylon), polyesters, polystyrene, polyacrylates, vinyl polymers (e.g., polyethylene, polytetrafluoroethylene, polypropylene and poly vinyl chloride), polycarbonate, polyurethane, poly dimethyl siloxane, cellulose acetate, poly methyl methacrylate, ethylene vinyl acetate, poly sulfone, nitrocellulose and similar copolymers. These synthetic polymeric materials can be woven into a mesh to form a matrix or substrate. Alternatively, the synthetic polymer materials can be molded or cast into selected forms. Purified biological polymers that can be appropriately formed into a substrate include polysaccharides (e.g., cellulose and starch), polyamino acids, collagen, gelatin and cat gut sutures.

B. Calcification Inhibitors

Biological materials and polymeric materials are susceptible to calcification to varying degrees depending on the composition and structure of the material. The mechanism of calcification is not completely understood, but it displays similarities to calcium deposition related to bone formation. It has been postulated that phosphatases, especially alkaline phosphatase, play a significant role in the pathological calcification process. See, R. J. Levy et al., 25 J. Biomedical Materials Research 905–935 (1991)

The invention involves the delivery of anti-calcification agents in a controlled manner at the cellular level within and around the particular bioprosthesis. Small total quantities of active agent can be delivered while being effective to reduce or inhibit calcification. While the quantities may be small, and therefore, for example, non-toxic relative to the recipient, they can represent relatively high loading relative to the local environment of the bioprosthesis containing the active compositions.

Calcification inhibiting agents include compounds that inhibit nucleation of calcification, as well as alkaline phosphatase inhibitors. See, U.S. Pat. No. 5,368,608 to Levy et al. The anti-calcification agent is preferably released over an extended period of time in order to significantly extend the useful life of the bioprosthesis. The release of the agent or agents above background concentrations would preferably extend over several months, and would more preferably extend over several years.

$Al^{+3}$, $Mg^{+2}$ and $Fe^{+3}$ ions have been demonstrated to be calcification inhibitors and, when delivered in a timed release fashion, are effective in reducing calcification of bioprostheses. Multivalent cations, such as $Ga^{+3}$, $La^{+3}$ etc., are also known to inhibit the function of enzymatic precursors to hydroxyapatite formation, such as alkaline phosphatase. The invention involves the controlled association and slow release of calcification inhibitors, including multivalent cations, within the biocompatible material.

$Be^{+2}$ ions are also known to inhibit phosphatase, although beryllium is relatively toxic. Other phosphatase inhibitors include phosphate ions, $Ga^{+3}$, $La^{+3}$, borate ions, oxalate ions, cyanide ions, L-phenylalanine, urea, excess $Zn^{+2}$, glycine, propylamine, lavamisole and arsenate ions. The functioning of alkaline phosphatase is also affected by the Mg/Zn ion ratios. Other calcification inhibitors include diphosphates.

C. Exogenous Storage Structures

Storage structures are used for the storage and slow release of calcification inhibiting agents. The storage structures preferably will be microscopic, macromolecular compositions, such as natural or synthetic proteins or appropriate synthetic polymers. It is to be understood, however, that aggregations of the preferred compositions need not be microscopic. The agents stored by the exogenous storage structures generally can be any calcification inhibiting agent, such as multivalent metal cations. The term "protein" is intended to mean not only amino acids linked by peptide linkages, but also conjugated proteins containing amino acids with carbohydrates, nucleic acids and/or lipids.

Biological materials treated with significant concentrations of $Al^{+3}$ cations in solution have associated $Al^{+3}$ cations. It is possible that the observed association of the $Al^{+3}$ cations with the natural biological substrates may be due to binding with naturally occurring ferritin. Ferritin is an iron storage protein that can store relatively large quantities of iron ions, several thousands of iron ions per protein molecule. Ferritin can also store similar but smaller quantities of $Al^{+3}$ and other non-ferrous ions. Naturally occurring ferritin may be crosslinked or otherwise bound to a protein or other biological or synthetic substrate during fixation.

The natural ferritin would very slowly release cations, such as $Al^{+3}$, $Fe^{+3}$, $Mg^{+2}$ or the like, into the local environment. The storage structures of the present invention are in addition or as an alternative to any naturally occurring structures, such as ferritin already present in the biocompatible material (endogenous ferritin). In this way, the effectiveness of the treatment can be enhanced through the use of storage structures supplied from external sources (exogenous storage structures such as exogenous ferritin).

Appropriate protein storage structures within the scope of the present invention include metal binding proteins such as ferritin, transferrin, hemoglobin, metalothien, myoglobin, ceruloplasmin and hemocyanin as well as modified proteins with addition of bifunctional chelators to generate metal binding capability. Ferritin is the preferred metal binding protein because of its large storage capacity. Apoferritin (ferritin protein without bound metal) is a 24 subunit protein with a molecular weight of approximately 450,000, although the molecular weight varies depending on the species from which the ferritin was isolated. Isoferritins, related proteins with differing numbers of subunits, are also within the scope of the present invention.

The ferritin core can store between about 2000 and about 4500 iron ions. For example, horse spleen ferritin can bind about 4500 iron ions compared with about 2500 iron ions in human ferritin. The iron is stored within the core as ferric oxide or ferric hydroxyphosphate. Ferritin can also bind large quantities of other metal ions including ions of the following metals: Al, Mg, Be, Cu, Zn, V, Tb, Cd. Binding of these non-iron ions is enhanced by the simultaneous binding of a moderate quantity of iron ions. The binding of iron or non-iron metal ions occurs both in vitro and in vivo. Generally, storage structures can be bound to tissue preloaded in vitro or loaded with cations in vivo, such as with iron ions from the blood supply.

The selection of a particular storage structure can be based on its storage capacity and the release rate of the stored calcification inhibitor. For example, ferritin or other metal binding proteins generally need not be saturated in the metal ion of interest to be useful in the invention. The ferritin can be charged with, for example, $Al^{+3}$ by incubating purified ferritin with a relatively concentrated $AlCl_3$ solution. The binding to the protein can be accelerated by heating and by pH adjustment. After a sufficiently long incubation, the free metal can be removed by passing the solution over an ion exchange resin or through a size exclusion membrane.

Instead of using a naturally occurring metal storage protein, other proteins can be modified to create metal binding capability. Preferred proteins have high molecular weight, such as immunoglobulins. Metal sequestering compounds can be covalently bonded to the protein.

Significant metal binding capability can be created by binding a bifunctional chelator, such as a polyaminocarboxylate or a polyaminophosphonate, to the protein as the metal sequestering compound. Preferred bifunctional chelators include electrophylic and nucleophilic moieties such as bromoacetamide, maleimide, inidoester, thiophthalimide, N-hydroxysuccinimyl ester, pyridyl disulfide, phenyl azide, o-acylisourea, diazonium hydrazine, carbonyl hydrazine, amino hydrazine, acyl hydrazine, diazonium semicarbazide, carbonyl semicarbazide, amino semicarbazide, acyl semicarbazide, thio semicarbazides and cyclic polyaminocarboxylates and cyclic polyaminophosphonates having 12 to 16 atom rings. The specific chelator can be selected to produce a desired release rate of the bound metal ions.

The bifunctional chelators generally can be covalently bonded to the protein by conventional methods. Typically, the covalent bonds will be formed between selected amino acid residues of the protein and a specific functional group in the chelator. The number of chelating agents bound to a protein will depend on the structures and the reaction conditions.

It is preferable to have at least one bifunctional chelator bound to each protein, and it is more preferable to have multiple bifunctional chelators bound to each protein. Metal ions can be bound to the chelator either before, at the time of, or after the covalent binding of the chelator to the protein. The reaction conditions may influence the selected order of the process.

An alternative to use of a metal storage protein is use of a synthetic organometallic polymer to store metal cations. For example, alkaline solutions of ferric citrate can form a polymer having a core of ferric hydroxide with citrate surrounding the core. See, T. G. Spiro et al., 89 J. Amer. Chem. Soc. 5555–5559 (1967). Another example of an organometallic polymer is vinylferrocene, which contains a plurality of $Fe^{+2}$ ions between aromatic rings along a carbon chain. Selenium containing polyesters, polyamides, polyureas and polyurethanes are well known and are also suitable for the present invention. Generally, a large number of these organometallic polymers have been characterized, and can be selected based on the desired metal ion and release rate.

The appropriate exogenous storage structures are not limited to structures appropriate for the storage of metal ions. Anti-calcification agents, specifically phosphatase inhibitors, include non-metallic compounds. Preferred macromolecular storage structures for the storage of organic agents are synthetic polymers.

The desired calcification inhibiting compound can either be a monomer within the polymer chain or can be bonded to a side group of the polymer. Whether the desired compound is covalently or noncovalently bound to the polymer, the polymer can be designed to degrade to yield the desired compound at a selected rate. The degradation can take place through a thermal process or through the interaction with the in vivo chemical and biochemical environment.

D. Binding of the Exogenous Storage Structures

Binding of the exogenous storage structures to the biocompatible material can involve specific binding interactions to target specific structures within the material. Alternatively, the binding can involve non-specific binding due, for example, to reaction with general crosslinking agents. The use of general crosslinking agents generally precludes exogenous storage structures from being concentrated at particular locations within the bioprosthetic material. The binding of the exogenous storage structures preferably takes place at near physiological pH, preferably ranging from about a pH of 6 to a pH of 8.5 and more preferably between a pH of 7.0 and a pH of 8.0.

A typical example of a procedure for non-specific binding makes use of glutaraldehyde, which crosslinks proteins by way of its two aldehyde groups. The non-specific crosslinking to bind the exogenous storage structures to the bioprosthetic material can be performed simultaneously with the fixation of the tissue. Alternatively, the non-specific crosslinking to bind the exogenous storage structures can be performed as a separate step before or after the completion of the fixation process.

The targeting of particular locations can be useful since it has been observed that calcification tends to initiate in specific locations. Examples of suitable targets include nuclear membranes, cytoplasmic locations, plasma membranes and extracellular sites.

The character of the targeted binding can be covalent or can involve a plurality of non-covalent interactions such as hydrogen bonding, van der Waals interactions and molecular rearrangements, which characterize, for example, antibody-antigen, specific binding protein-receptor and enzyme-substrate associations. A preferred method of targeting a particular location involves covalent binding of a linker to the storage structure and association of the linker with the bioprosthetic material by a plurality of non-covalent interactions.

A variety of commercially available antibodies and other specific binding reagents may be used as linkers, i.e., targeting molecules, to target cellular or extracellular sites having certain specific receptors. Alternatively, cellular or extracellular components at a preferred location of a biological material can be isolated by conventional techniques. For example, nuclear membranes or a specific portion of the nuclear membrane corresponding to an antigen or groupings of antigens can be isolated. The isolated materials then are used to produce polyclonal or monoclonal antibodies by conventional techniques. The resulting antibodies are covalently bonded to the exogenous storage structure to prepare it for binding to the bioprosthetic material.

A storage structure having an attached antibody, or comparable targeting molecule is considered a "storage structure" for the purposes of the present application. The binding of compounds to antibodies is well established in the art, especially where the compound is a protein. Due to its high iron content, ferritin is commonly linked to antibodies to serve as an electron microscopy probe in the histology field. In a preferred embodiment, glutaraldehyde is used to crosslink the respective proteins, i.e., ferritin and immunoglobulin.

The present inventors have demonstrated that calcification initiates frequently in the vicinity of the nuclear membrane. Therefore, a preferred approach involves use of antibodies directed to the nuclear membrane or a portion of the nuclear membrane. In this way, the storage structures can be targeted to cellular structures particularly susceptible to early events of calcium deposition.

E. Combined Treatment

The binding of exogenous storage structures of the invention can be combined with the process of direct treatment with metal salt solutions. Metal salt concentrations of the salt solutions generally are between 0.00001 and 0.1 molar, and preferably between 0.001 and 0.1 molar. The contacting of the biocompatible material with the metal salt solutions can take place before, after or during the binding of the storage structures to the biocompatible material. For in vivo loading, the supply of necessary ions, such as iron, could be provided by the host's blood supply. Appropriate salts include without limitation aluminum chloride, aluminum chlorate, aluminum lactate, aluminum potassium sulfate, aluminum nitrate, ferric chloride, ferric nitrate, ferric bromide, ferric sodium edentate, ferric sulfate, and ferric formate.

The metal salts also can be incorporated into a polymer matrix used in the bioprosthesis. The metal salts are preferably added during the polymerization step such that they are incorporated into the polymer matrix. In this way, the calcification inhibitor is released at a controlled rate over an extended period of time. The exogenous storage structures are then bonded to the polymer matrix.

Calcium ion chelators preferably at concentrations between approximately 0.00001 M and approximately 0.1 M can be added to the metal salt solutions prior to treatment. For example, citrate salts and citric acid have been found to enhance synergistically the calcification inhibition effect of $Al^{+3}$ and $Fe^{+3}$ ions. similarly, other calcium ion chelators such as diphosphonate salts, including without limitation ethanehydroxydiphosphonate (EHDP or etidronate) and aminopropanehydroxydiphosphonate, also produce a synergistic improvement in the anti-calcification effect of the $Al^{+3}$ and $Fe^{+3}$ ions. Higher or lower concentrations can be used in particular applications.

The selection of the exogenous storage structure may be effected by the combined treatment with metal salt solutions. For example, the release rate of a calcification inhibiting agent may be selected in the combined treatment to yield more effective inhibition or inhibition over a longer period of time.

F. Using Endogenous Proteins for Delivery of Cations

In the same way that exogenous proteins can be modified to create metal binding capability, endogenous proteins can be similarly modified. For example, the biocompatible materials can be bound to bifunctional chelators to store metal ions. Preferred bifunctional chelators include electrophylic and nucleophilic moieties such as bromoacetamide, maleimide, inidoester, thiophthalimide, N-hydroxysuccinimyl ester, pyridyl disulfide, phynyl azide, o-acylisourea, diazonium hydrazine, carbonyl hydrazine, amino hydrazine, acyl hydrazine, diazonium semicarbazide, carbonyl semicarbazide, amino semicarbazide, acyl semicarbazide, thio semicarbazides and cyclic polyaminocarboxylates and cyclic polyaminophosphonates having 12 to 16 atom rings. The specific chelator can be selected to produce the desired release rate of the bound metal ions.

The bifunctional chelators can be covalently bound to the endogenous proteins in the same way they would be bound to the exogenous proteins as described above in section C. The quantities of bifunctional chelators bound to the biocompatible materials can be selected to achieve the desired loading of calcification inhibitors in the material.

EXAMPLE

This example demonstrates the calcification inhibiting effect of crosslinking ferritin loaded with aluminum chloride to bioprosthetic material.

Horse spleen ferritin (HS ferritin) was obtained from Sigma Chemical Company (Saint Louis, Mo.). A 0.25 ml quantity of a 100 mg/ml solution of HS ferritin was added to a test tube along with 1 ml of 0.1 M aluminum chloride hexahydrate solution that also contained 0.025 g of $KH_2PO_4$. The test tube was covered with foil and placed in an incubator at 68.2° C. for 23 hours shaking at 150 RPMs. A total of 54 tubes were prepared.

Following the 23 hours of shaking, the ferritin was dialyzed using a 10,000 Dalton pore dialysis membrane (Spectra Pour) against a HEPES buffer solution. Dialysis was continued until aluminum levels were considered baseline using atomic emission spectroscopy. Approximately 250 aluminum ions were bound per ferritin molecule, indicating the ferritin was not saturated with $Al^{+3}$ ions. Then, the dialysis tubing was placed in a 0.050 M phosphate buffered saline solution until ready for use.

Porcine aortic heart valves were obtained from a standard supplier, which followed USDA guidelines for slaughtering the animals. The valves were dissected, and tissue samples were prepared from all the leaflets and from random 8 mm root biopsy punches. The leaflets had a dry weight of about 10 mgs, and the root tissues had a dry weight of about 20 mgs. Each tissue sample was placed in individual dialysis bags containing aluminum loaded ferritin. The dialysis bags containing the samples then were placed in 0.5 percent glutaraldehyde solutions buffered with 0.050 M HEPES biological buffer (pH 7.4) (Sigma Chemical Co., Lot 75H5716) at room temperature for about one week. Comparable samples were prepared with HS ferritin without aluminum loading the ferritin.

To determine delivery of cations in vitro, ferritin treated root and leaflet tissue samples were placed in HEPES for approximately 406 hours at room temperature. The resulting solution was analyzed for aluminum and iron cations using ICP-AES (Inductively Coupled Plasma—Atomic Emission Spectroscopy). Trace amounts of both cations (about 0.01 to 0.35 ppm) were found in the solution.

An in vivo study was performed to determine the ability of the treated tissue samples to resist calcification. Both ferritin-treated and aluminum-loaded-ferritin-treated, leaflet and root tissue samples were used in the study. A total of nine treated samples of each of the four types were used for a total of 36 treated samples. In addition, eighteen control tissue samples were used, of which nine were porcine aortic leaflet tissues and nine were porcine aortic root tissues. The control samples were crosslinked with 0.5 percent glutaraldehyde solution buffered with HEPES buffer prior to the in vivo study. Samples were handled using aseptic technique to prevent contamination.

The 36 treated samples and 18 control samples were placed subcutaneously in the backs of juvenile male rats using color coded suture. Of the nine duplicate samples of each type, three were removed 21 days after implantation and the other six were removed 63 days after implantation. Following removal, the samples are placed in 0.9 percent saline (NaCl in $H_2O$) prior to analysis.

Each tissue sample was removed from the saline and sectioned in half. One half portion of the tissue sample was cleaned of host (i.e., rat) tissue and used for elemental analysis. The second half portion of the tissue sample was placed in 10 percent formalin and stored for histological examination.

Elemental analysis of the recovered tissue is performed by first drying the tissue. The dried tissue is dissolved in concentrated nitric acid. The resulting solution is subjected to ICP-AES.

Values from the elemental analysis measurements are compiled in the following table. These values are averages of 3 measurements (21 days) or 6 measurements (63 days).

|  |  | Calcium mg/g | | Calcium mg/g | |
| --- | --- | --- | --- | --- | --- |
| Sample Group | Tissue Type | 21 days | Std. Deviation | 63 days | Std. Deviation |
| Aluminum loaded Ferritin Treatment | Leaflet | 2.86 | 0.81 | 9.88 | 17.24 |
|  | Root | 0.97 | 0.2 | 2.05 | 3.18 |
| Ferritin Treatment | Leaflet | 16.72 | 7.34 | 63.45 | 34.9 |
|  | Root | 9.33 | 3.39 | 60.61 | 31.39 |
| Control | Leaflet | 144.27 | 20.67 | 213.00 | 43.96 |
|  | Root | 52.44 | 0.54 | 131.26 | 22.84 |

These results show a reduction of calcification after 21 days of implantation to about 2.0% and 1.8% for the leaflet and root tissues, respectively, following treatment with aluminum loaded ferritin. Following ferritin treatment, calcium levels were reduced to 11.6% and 17.8% for the leaflet and root tissues, respectively. After 63 days (approximately two months) of implantation, reductions in calcification to 4.6% and 1.6% are observed for leaflet and root tissue, respectively, following treatment with aluminum loaded ferritin. Calcium levels were reduced to 29.8% and 46.2% for the leaflet and root tissues, respectively, following 63 days of implantation. Thus, significant reduction in calcification due to native (partially iron-loaded) ferritin and, especially, aluminum-loaded ferritin was demonstrated.

What is claimed is:

1. A bioprosthetic article comprising a biocompatible material forming at least a portion of said bioprosthetic article and a plurality of exogenous storage structures that are bound to the biocompatible material by covalent bonds, antibody-antigen associations, specific binding protein-receptor associations or enzyme-substrate associations, said exogenous storage structures comprising natural macromolecules selected from the group consisting of proteins, carbohydrates and nucleic acids that are in addition or as an alternative to any naturally occurring structures and said exogenous storage structures collectively having greater than about 0.5 mg metal cations per gram of biocompatible material releasably bound thereto.

2. The bioprosthetic article of claim 1, wherein said storage structures collectively have greater than about 10.0 mg metal cation per gram of biocompatible material.

3. The bioprosthetic article of claim 1, wherein said storage structures collectively have greater than about 15.0 mg metal cation per gram of biocompatible material.

4. The bioprosthetic article of claim 1, wherein said metal cations comprise $Al^{+3}$, $Fe^{+3}$, or mixtures thereof.

5. The bioprosthetic article of claim 1, wherein said metal cation comprises $Al^{+3}$ cations.

6. The bioprosthetic article of claim 1, wherein said storage structures comprise ferritin.

7. The bioprosthetic article of claim 1, wherein said biocompatible material comprises mammalian tissue.

8. The bioprosthetic article of claim 7, wherein said natural tissue is selected from the group consisting of heart valves, roots, walls, leaflets, pericardial tissue, cartilage bypass grafts, tendons, ligaments, skin patches, blood vessels and umbilical tissue.

9. The bioprosthetic article of claim 1, wherein said biocompatible material comprises a tissue engineered material.

10. The bioprosthetic article of claim 1, wherein said biocompatible material comprises porcine heart valves or portions thereof.

11. The bioprosthetic article of claim 1, wherein said biocompatible material comprises bovine pericardium.

12. A bioprosthetic article comprising natural tissue and a plurality of exogenous storage structures that are bound to said natural tissue by covalent bonds, antibody-antigen associations, specific binding protein-receptor associations or enzyme-substrate associations, said storage structures comprising natural macromolecules selected from the group consisting of proteins, carbohydrates and nucleic acids that are in addition or as an alternative to any naturally occurring structures, said storage structures having a quantity of calcification inhibitors releasably bound thereto, and said natural tissue having calcium deposition reduced by greater than about 95 percent relative to equivalent natural tissue without said bound exogenous storage structures after approximately two months of subcutaneous implantation within a mammal.

13. The bioprosthetic article of claim 12, wherein said natural macromolecule comprises ferritin.

14. The bioprosthetic article of claim 13, wherein said calcification inhibitor comprises $Al^{+3}$ cations.

15. The bioprosthetic article of claim 12, wherein said biocompatible material comprises porcine heart valves or portions thereof.

16. A method of producing a bioprosthetic article comprising the step of binding ferritin to natural tissue, where said ferritin is loaded with calcification inhibiting metal cations such that there are at least 0.5 mg of metal cations per gram of said natural tissue.

17. The method of claim 16, wherein said metal cations comprise $Al^{+3}$ cations.

18. The method of claim 16, wherein said binding is accomplished by covalent or noncovalent bonding of said ferritin to said natural tissue.

19. The method of claim 18, wherein said bonding is performed by contacting said loaded ferritin and said natural tissue with a solution comprising glutaraldehyde.

20. The method of claim 18, wherein said bonding is performed by forming antibody-antigen linkages.

21. The bioprosthetic article of claim 1 wherein said exogenous storage structure comprises a metal binding protein.

22. The bioprosthetic article of claim 12 wherein said exogenous storage structure comprises a metal binding protein.

23. The bioprosthetic article of claim 1 wherein said exogenous storage structure is selected from the group consisting of ferritin, transferrin, hemoglobin, metalothien, myoglobin, ceruloplasmin, hemocyanin, isoferritin, and modified proteins with added bifunctional chelators.

24. The bioprosthetic article of claim 12 wherein said exogenous storage structure is selected from the group consisting of ferritin, transferrin, hemoglobin, metalothien, myoglobin, ceruloplasmin, hemocyanin, isoferritin, and modified proteins with added bifunctional chelators.

* * * * *